United States Patent
Kullenberg et al.

Patent Number: 6,151,379
Date of Patent: Nov. 21, 2000

[54] METHOD AND DEVICE FOR MEASURING DENSITY

[76] Inventors: Ragnar Kullenberg, Sandvägen 4, SE-310 42 Haverdal; Anders Ullberg, Berghållavägen 4, SE-616 33 Aby, both of Sweden

[21] Appl. No.: 09/155,042
[22] PCT Filed: Mar. 20, 1997
[86] PCT No.: PCT/SE97/00464
  § 371 Date: Sep. 17, 1998
  § 102(e) Date: Sep. 17, 1998
[87] PCT Pub. No.: WO97/35175
  PCT Pub. Date: Sep. 25, 1997

[30] Foreign Application Priority Data

Mar. 21, 1996 [SE] Sweden .................... 9601083

[51] Int. Cl.⁷ .................................................. G01B 15/02
[52] U.S. Cl. ............................. 378/54; 378/53; 378/55; 378/102; 378/88
[58] Field of Search ........................... 378/54, 55, 102, 378/53, 88

[56] References Cited

U.S. PATENT DOCUMENTS

| | | |
|---|---|---|
| 3,136,892 | 6/1964 | Willet et al. . |
| 4,150,297 | 4/1979 | Borggren . |
| 4,228,353 | 10/1980 | Johnson . |
| 5,023,805 | 6/1991 | Aune et al. . |
| 5,331,163 | 7/1994 | Leahey et al. . |

FOREIGN PATENT DOCUMENTS

| | | |
|---|---|---|
| 0236623 | 9/1987 | European Pat. Off. . |
| 1250743 | 10/1989 | Japan . |
| 9419681 | 9/1984 | WIPO . |

*Primary Examiner*—David V. Bruce
*Assistant Examiner*—Pamela R. Hobden
*Attorney, Agent, or Firm*—Orum & Roth

[57] ABSTRACT

The present invention relates to a device for measuring density or determining the presence and the amount of materials of different density in an object to be measured, of a solid, liquid or gaseous material, said device comprising at least one source of radiation for emitting electromagnetic radiation, and at least one sensor for measuring the radiation intensity, so positioned as to absorb radiation form the source of radiation and being connected to a calculation unit. In accordance with the invention the device emits radiation of at least two wavelenghts and comprises measurement means for determination of the extension of the object between the source of radiation and the sensor. In addition, the invention relates to a method of measuring density, comprising radiating electromagnetic rays through an object to be measured and measuring the radiation intensity on the ray-exit side of the object to be measured. In accordance with the method the extension of the object is measured along the path of the radiation through the object to be measured and the radiation is effected at least at two different wavelenghts.

7 Claims, 2 Drawing Sheets

METHOD AND DEVICE FOR MEASURING DENSITY

TECHNICAL FIELD

The present invention relates to a method and device for measuring density and for distinguishing areas of different density in an object to be measured, of a solid, liquid or gaseous material, said device comprising a source of radiation emitting electromagnetic radiation, a sensor for measuring the radiation intensity after passage through the object to be measured, and a calculation unit.

BACKGROUND

In many cases it is of interest to be able to measure the density of materials without damaging or changing it, and to be able to determine the presence and the amounts of materials having different densities. For instance, within the forest industry the possibility of distinguishing between different qualities is becoming increasingly important. Already at the felling stage it is important to know the density of the logs, on the one hand in order to be able to directly detect and to reject parts that are decayed or otherwise damaged and consequently without value, and on the other to be able to calculate the price of the timber (which at least in Sweden nowadays is set on the basis of density and not on volume). Also in sawmills density measuring is of interest. Improved knowledge of logs makes log classification easier, allowing sorting-out of damaged logs or logs exhibiting too many knots or being resinous.

Also in other branches measurements of this type may be of great importance. For instance, they make it easy to determine the quality of oil in order to estimate the amount of water, metal impurities and other components contained therein, which is important in order to allow engine oil changes to be performed at sufficiently frequent intervals and to prevent wear and breakdown. In addition, the method may be used in the handling of waste to be sorted according to type, to determine the quality of building elements, and so on.

For the purpose of measuring density, it has been known for a long time to allow electromagnetic radiation to penetrate an object to be measured and thereafter to measure the intensity and to calculate the amount of the original intensity that has been absorbed. Examples of such methods and devices are found in SE 466 365, DE 28 46 702, U.S. Pat. No. 3,136,892 and U.S. Pat. No. 5,105,453. Without exception, radiation of one wavelength only is used in these examples, and consequently one obtains only one indication of the radiation intensity along each radiation path through the object to be measured. This indication may be used to determine the mean density of the object to be measured and changes thereof along the object but not to distinguish the presence of and the amount of different types of materials upon each measurement. In accordance with the examples given such information may be gained only from a large number of radiation paths that depart from different points (tomography).

OBJECT OF THE INVENTION

The object of the subject invention is to provide a device and a method for measuring density, allowing the presence and the amount of different types of materials to be determined in a convenient and simple manner. This object is achieved by means of a device and a method defined in the appended claims.

DESCRIPTION OF PREFERRED EMBODIMENTS

Two presently preferred embodiments will be explained in the following for exemplifying purposes and with reference to the accompanying drawings.

Figure 1:
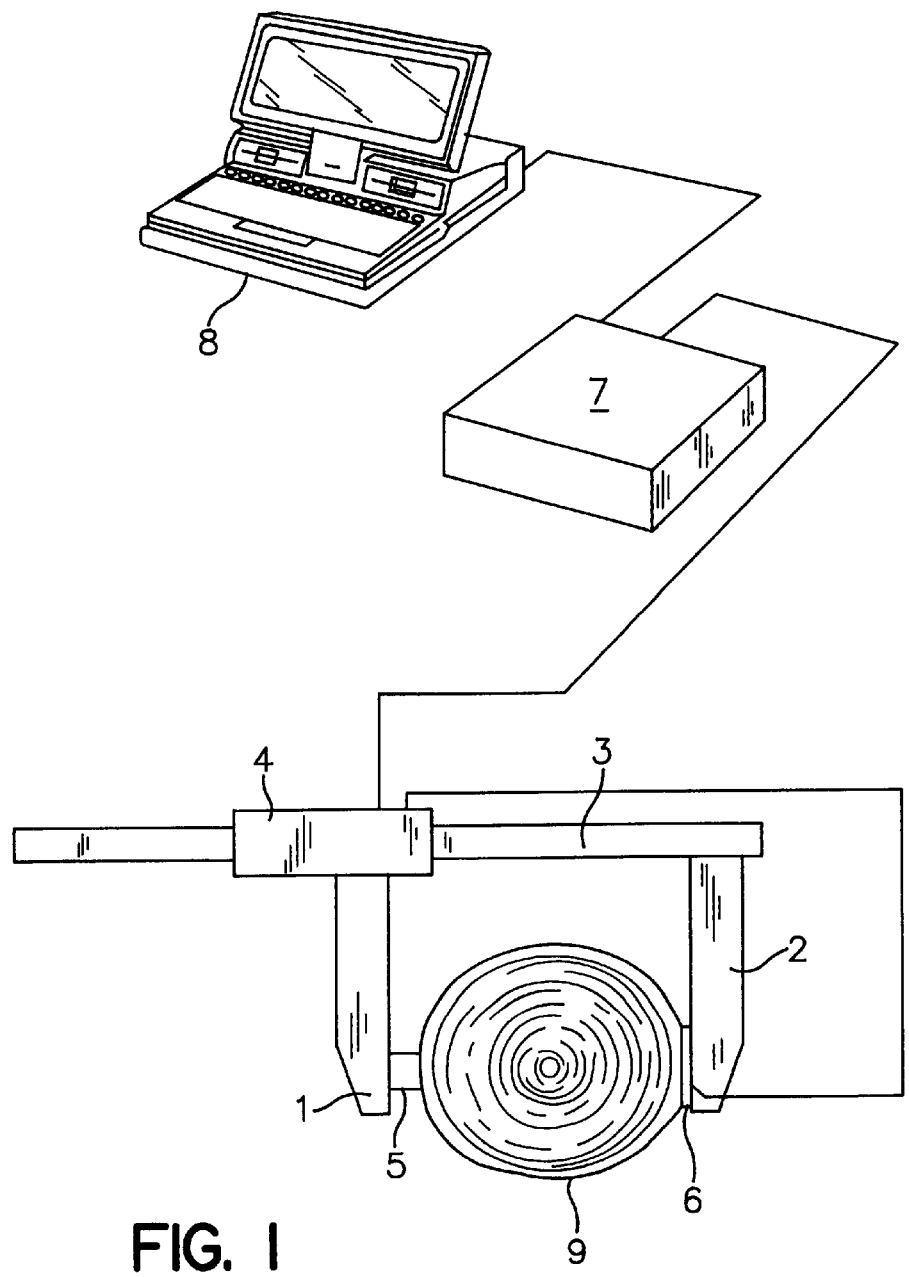
FIG. 1 is a schematic view of a mobile variety of the inventive object for density measurement and determination of the presence and the amount of different density areas in logs.

FIG. 1 illustrates a mobile device for measuring the density of logs in accordance with the invention. The device comprises two arms 1, 2 which are movably connected in a manner allowing readings to be made with respect to the distance between two predetermined points, one on each arm. The arms could for instance be joined together in the manner illustrated in FIG. 1, according to which figure the arms 1, 2 are attached to a principal piece 3 in the manner of shank arms, such that one 2 of the shank arms is rigidly connected with the principal piece whereas the opposite arm 1 is movably joined to the main piece 3, via an interconnection piece 4. In this manner calipers are formed by means of which the position of the interconnection piece 4 relative to the main piece 3 may be read to establish the spacing between the arms 1, 2. The reading may be made manually but preferably should be made automatically, whereupon the result by way of electrical wires is forwarded to a measurement interface 7 and from there further to a calculating unit 8. However, the measurement caliper may have a different configuration. The arms could for instance be pivotable relative to one another, whereupon the angle that the arms form between them may be converted to establish the distance between two points, one on each arm 1, 2.

One of the arms 1, 2 supports a source of radiation on the end thereof that is not joined to the main piece 3. The source of radiation is intended to emit electromagnetic radiation, preferably within the x-ray range and having at least two different wavelengths. The emission may be made sequentially, i.e. the source of radiation 5 initially emits rays having one wavelength and then, by altering the tension across the radiation tube, a different wavelength. Alternatively, the source of radiation 5 may consist of two or several separate juxtaposed radiation tubes which radiate either simultaneously or sequentially. The important thing is, however, that the different-wavelength radiation traverses the object to be measured along essentially the same path. The other arm 2 supports a sensor 6 for measuring the intensity of the radiation emitted by the source of radiation. The sensor 6 may consist of several independent part sensors. When radiation of two (or more) wavelengths is emitted simultaneously from the source of radiation 5 the intensity of the two signals must then be measured individually. This may be effected directly by making provisions such that certain part sensors by filtration only measure radiation having a certain energy level while others measure other energy levels. It may also be effected by subsequent treatment of signals, allowing superimposed signals to be separated. The measurement results are conveyed further to the measurement interface 7 and from there to the calculating unit 8. The measurement interface 7 according to FIG. 1 comprises a source of tension for the source of radiation 5. In a manner to be described in closer detail in the following the calculating unit 8 may then compute the presence of and the amount of different types of materials.

In use, the calipers are clamped about an object 9 to be measured, whereupon the diameter of the object is read and the measurement data thus obtained are transferred to the calculating unit 8. The source of radiation 5 is then activated, the radiation energy penetrating through the object 9 to be measured and reaching the sensor 6. The sensor registers the intensity of the incident radiation and the resulting data are also transferred to the calculating unit 8 which computes and presence the end results.

The advantage encountered by this embodiment of the device is that it may be connected to e.g. logging machines in a very simple manner, allowing the driver to determine directly, in the driver's cabin, the quality of a tree trunk in question. In this way he may establish whether the trunk suffers from internal rot or is otherwise decayed, and the degree of density of the wood material, and he is also able to gain other information of interest, already at the logging stage. In addition, it is advantageous to use x-ray radiation of an energy level that penetrates the objects 9 to be measured but which also minimizes the risk to handling personel exposed to radiation.

Figure 2:
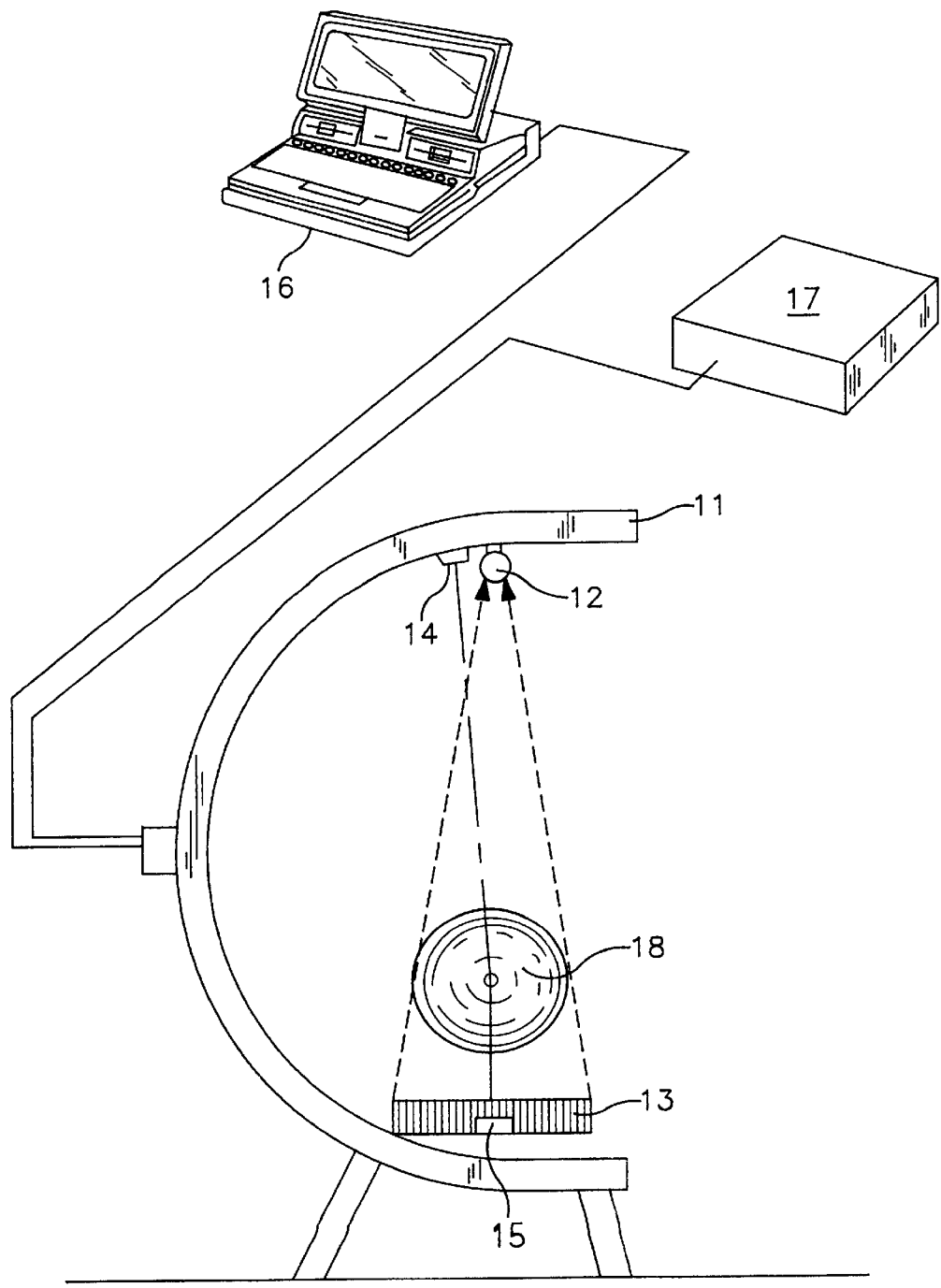
FIG. 2 is a schematic view of a stationery variety of the inventive object for corresponding density measurement.

Another, stationary embodiment is illustrated in FIG. 2. In the stationary device the source of radiation 12 and the sensor 13 are mounted on a frame 11. Preferably, the frame 11 extends around an object 18 to be measured. The frame 11 may be configured as a protective shield around the source of radiation 12 in order to reduce the radiation hazards to the personnel in the vicinity, and preferably it consists of a radiation-absorbing material, such as lead. The source of radiation 12 and the sensor 13 may be configured in a manner equivalent to the embodiment of FIG. 1. Alternatively, the sensor 13 may have a larger extension allowing reception of radiation from a larger number of radiation paths. In this manner the entire object 18 to be measured may be irradiated and measured directly, instead of measurement being effected along one path of radiation only through the object to be measured. The measurement data from the sensor 13 are transferred to the measurement interface 17 and to a calculating unit 16, and the power unit and generator relating to the source of radiation are designated by reference 17 in FIG. 2.

For use within e.g. the pulp and sawmill industries the objects to be measured suitably are moved past the measurement equipment on a conveyor belt or the like.

Optionally, the source of radiation 12 could also be divided into several spaced-apart radiation tubes including associated sensors 13 which are activated at the pace of movement of the object 18 to be measured, whereby the radiation path through the object 18 to be measured still essentially is the same.

In order to determine the extension of the object 18 to be measured and thus the length of the radiation path through the object to be measured lasers 14, 15 are used in accordance with the shown embodiment. The lasers emit laser pulses against the object 18 to be measured on either side thereof in the area intended to be penetrated by the radiation energy. By measuring the time required for the laser pulses to be reflected from the object 18 to be measured it is possible to compute the distance, and thus the extension of the object being measured. However, alternative methods of measuring the extension of the object 18 to be measured obviously are possible, such as mechanical measurement, measurement by radiation, using parallel rays that do not penetrate the object to be measured, such as ordinary light, light-sensitive sensors, and so on.

Various methods of measuring with the aid of devices in accordance with the invention will be described in the following. As already mentioned at least three measurements are performed, viz. the length of the path of radiation through the object is measured as is also the intensity of radiation emitted at least at two different wavelengths, after the penetration of the radiation energy through the object to be measured. The radiation energy will be absorbed to a certain extent in the object whereby the intensity is reduced. The magnitude of the reduction depends on the one hand on the length of the path through the object, and on the other on the nature of the material of the object. The material dependency aspect is based on the fact that the characteristics of the attenuation coefficient differ for different materials. In addition, the attenuation coefficient of each individual material depends on the wavelength of the radiation, and this dependency differs in different materials. Consequently, the following equations may be set up with respect to the intensity of radiation measured after penetration through the object to be measured:

$$N_1 = N_{0,1} \exp(-\mu_{1,1} t_1 - \mu_{2,1} t_2 - \mu_{3,1} t_3)$$

$$N_2 = N_{0,2} \exp(-\mu_{1,2} t_1 - \mu_{2,2} t_2 - \mu_{3,2} t_3)$$

wherein $N_1$ is the measured radiation intensity after passage through the object to be measured with respect to wavelength level 1, $N_{0,1}$ is the measured radiation intensity with respect to wavelength level 1 without passage through the object, $\mu_{x,1}$ is the mass attenuation coefficient (attenuation coefficients divided by the density of the material) with respect to each material x and the wavelength level (cm$^2$/g) and $t_x$ is the thickness of the material x as measured in mass per unit of area (g/cm$^2$), wherein the index 1 above in this case ranges from 1 to 2 and index x from 1 to 3.

Because the length of the path of radiation through the object to be measured is known, the following equation may also be set up:

$$T = \frac{t_1}{\rho_1} + \frac{t_2}{\rho_2} + \frac{t_3}{\rho_3}$$

wherein T is the total thickness (cm) and $\rho_1$ is the density of material 1, 1 in this case ranging from 1 to 3. With the aid of these three equations and because the densities and the attenuation coefficients of the materials included are known it becomes possible to determine the presence and the amounts of these materials. In accordance with this example involving measurement at two wavelengths, resulting in three equations it becomes possible to determine up to three unknown variables. Consequently, the method is suitable for analysing bodies to be measured comprising up to three different materials. To determine more complex systems, measurements may be carried out at a larger number of wavelength levels and generally speaking it is possible to determine, in the case of N measurements at different wavelengths, N+1 unknown variables.

Obviously, it is possible to instead use the measurement data to estimate the density of the object to be measured or variations in the object. In that case the attenuation coefficient of the materials included are used (instead of the mass attenuation coefficient), allowing the thicknesses to be measured in terms of units of length instead. In this manner advance knowledge of the densities of the materials included is not necessary.

Several varieties of the above described embodiments are of course conceivable. For instance, the device and the method in accordance with the invention may be configured in partly different ways, as already mentioned above, and in addition the device may be adapted for measurement of liquids, other types of solid materials, or gases. Such modifications of the invention must be regarded to fall within the scope of the invention as the latter is defined in the appended claims.

What is claimed is:

1. A device for measuring density or determining the presence and the amounts of materials of different density in an object, which object consists at least mainly of a solid material and has variable thickness, wherein attenuation coefficients are known for materials present in said object, said device comprising:

at least one source of radiation for emitting electromagnetic radiation, and at least one sensor for measuring the radiation intensity after passage through the object to be measured, and measurement means for determining an extension of the object between the source of radiation and the sensor, and a calculation unit, and radiation is emitted in at least two wavelengths, and the calculation unit calculates the presence and amount of different materials present on the basis of the attenuation coefficients, measurement data received from the sensor and the measurement means, and the number of materials calculable being the number of different radiation wavelengths emitted plus one.

2. A device as claimed in claim 1, wherein it is mobile and in that the measurement means comprises two interconnected arms (1, 2) arranged for relative movement and supporting the sensor (6) and the source of radiation (5), respectively, said sensor and said source of radiation being in communication, and in that said arms (1, 2) are arranged, owing to their mutual positions, to provide information on the extension of the object (9) to be measured when the arms (1, 2) are brought to a position of the closest possible proximity to one another on either side of the object (9) to be measured.

3. A device as claimed in claim 1, wherein it is stationary and in that the measurement means comprises lasers (14, 15) positioned in essentially opposite relationship adjacent to the source of radiation (12) and to the sensor (13), respectively, the beams of light emitted by the laser and reflected back from the object (18) being measured being used to calculate the thickness of the object (18).

4. A device as claimed claim 1, wherein the electromagnetic radiation is within the range of x-ray radiation.

5. A method of measuring density in an object, comprising radiating electro-magnetic rays through an object, and measuring the intensity of the electromagnetic rays on the ray-exit side of the object, wherein the object is composed of materials having known attenuation coefficients, and an extension of the object along the path of the electromagnetic rays is measured, effecting the electromagnetic rays at least at two different wavelengths, collecting data at each wavelength, on the basis of the measurement data, extension, and each materials' attenuation coefficients, calculating the presence and the amount of each material, said materials of a number equal to the number of different electro-magnetic wavelengths used plus one.

6. A device as claimed in claim 2, wherein the electromagnetic radiation is within the range of x-ray radiation.

7. A device as claimed in claim 3, wherein the electromagnetic radiation is within the range of x-ray radiation.

* * * * *